United States Patent [19]

Mentrup et al.

[11] 4,038,314
[45] July 26, 1977

[54] 1-HYDROXY-1-[(4'-HYDROXY-3'AMINOSULFONAMIDO)-PHENYL]-2-AMINO-ETHANES AND SALTS

[75] Inventors: Anton Mentrup, Ingelheim am Rhein; Kurt Schromm, Ingelheim am Rhein; Ernst-Otto Renth, Ingelheim am Rhein; Werner Traunecker, Munster-Sarmsheim, all of Germany

[73] Assignee: Boehringer Ingelheim GmbH, Ingelheim am Rhein, Germany

[21] Appl. No.: 453,438

[22] Filed: Mar. 21, 1974

Related U.S. Application Data

[63] Continuation-in-part of Ser. No. 239,311, March 29, 1971, abandoned.

[30] Foreign Application Priority Data

Apr. 1, 1971  Germany ............................ 2115926

[51] Int. Cl.² ..................... C07C 143/80; A61K 31/18
[52] U.S. Cl. ............................. 260/556 N; 424/321; 260/501.19
[58] Field of Search ... 260/556 N, 556 AR, 326.5 SF, 260/293.73

[56] References Cited
U.S. PATENT DOCUMENTS 3,574,741  4/1971  Gould et al. .............. 260/326.5 SF
3,701,808  10/1972  Hartley et al. .............. 260/556 AR
3,711,545  1/1973  Kaiser et al. .................... 260/556 N
3,804,834  4/1974  Mentrup et al. .............. 260/570.6 X
3,875,233  4/1975  Bastian et al. ................ 260/570.6 X

OTHER PUBLICATIONS

*Medicinal Chemistry*, Burger, Ed., 3rd Ed., Part II, pp. 1253-1257 (1969).

Primary Examiner—Daniel E. Wyman
Assistant Examiner—Thomas A. Waltz
Attorney, Agent, or Firm—Hammond & Littell

[57] ABSTRACT

Compounds of the formula

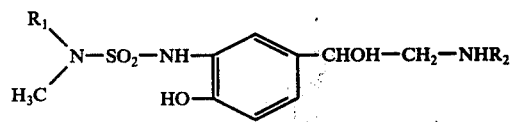

wherein $R_1$ is hydrogen or methyl, and
  $R_2$ is phenoxy-(alkyl of 2 to 3 carbon atoms), phenyl-(alkyl of 4 to 5 carbon atoms), hydroxyphenyl-(alkyl of 3 to 5 carbon atoms), or naphthyl-(alkyl of 4 to 5 carbon atoms);

and their non-toxic, pharmacologically acceptable acid additions salts; the compounds as well as the salts are useful as dilators of the peripheral blood vessels, as cardiotonics and as broncholytics.

5 Claims, No Drawings

1-HYDROXY-1-[(4'-HYDROXY-3'AMINOSULFONAMIDO)-PHENYL]-2-AMINO-ETHANES AND SALTS

This is a continuation-in-part of copending application Ser. No. 239,311, filed Mar. 29, 1971 now abandoned.

This invention relates to novel 1-hydroxy-1-[(4'-hydroxy-3'-aminosulfonamido)-phenyl]-2-aminoethanes and acid addition salts thereof, as well as to methods of preparing these compounds.

More particularly, the present invention relates to a novel class of compounds represented by the formula

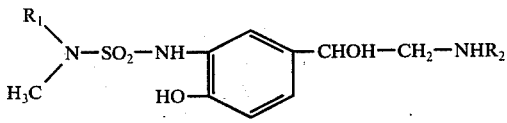

(I)

wherein $R_1$ is hydrogen or methyl, and
$R_2$ is phenoxy-(alkyl of 2 to 3 carbon atoms), phenyl-(alkyl of 4 to 5 carbon atoms), hydroxyphenyl-(alkyl of 3 to 5 carbon atoms), or naphthyl-(alkyl of 4 to 5 carbon atoms);

and their non-toxic, pharmacologically acceptable acid addition salts.

The compounds according to the present invention occurs as racemic mixtures, as diastereoisomeric antipode pairs and as optically active isomers.

Of particular interest are those compounds of the formula I
wherein $R_1$ is hydrogen or methyl, and
$R_2$ is phenoxy-(alkyl of 2 to 3 carbon atoms), phenyl-(alkyl of 4 to 5 carbon atoms), or naphthyl-(alkyl of 4 to 5 carbon atoms), and their non-toxic, pharmacologically acceptable acid addition salts.

Of more particular interest are those compounds of the formula I
wherein $R_1$ is methyl, and
$R_2$ is phenoxy-(alkyl of 3 carbon atoms) phenyl-(alkyl of 5 carbon atoms), or naphthyl-(alkyl of 5 carbon atoms), and their non-toxic, pharmacologically acceptable acid addition salts.

The compounds embraced by formula I above may be prepared by the following methods:

Method A

By splitting off the substituents $R_3$ and $R_4$ from a compound of the formula

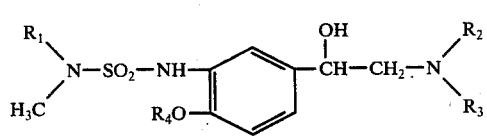

(II)

wherein $R_1$ and $R_2$ have the same meanings as in formula I, $R_3$ is a protective substituent which may be removed by hydrolysis or hydrogenation, $R_4$ is a protective substituent which may be removed by hydrolysis, hydrogenation, ester exchange or ether cleavage, and one of $R_3$ and $R_4$ may also be hydrogen.

Protective groups which may be removed by hydrogenation are primarily benzyl or substituted benzyl radicals. The removal of such groups is effected by hydrogenation in the presence of conventional hydrogenation catalysts, such as Raney nickel, platinum or palladium.

Examples of protective groups which may be split off by hydrolysis or by ester exchange with an alcohol are acetyl and benzoyl. Their removal is effected with water or by ester exchange with a lower alkanol in the presence of catalizing substances, such as acids or bases.

If $R_4$ is a group which may be removed by ether cleavage, such as alkyl or benzyl, the cleavage is effected with conventional ether cleaving agents, such as concentrated hydrohalic acids; benzyl and substituted benzyl groups may be removed especia;lly easily in this manner.

If $R_3$ and $R_4$ are both protective groups, they may be removed simultaneously or successively.

Method B

By reducing a ketone of the formula

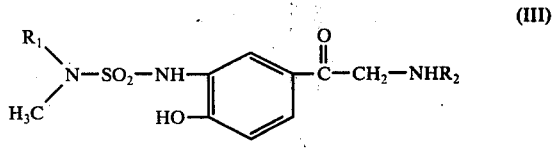

(III)

wherein $R_1$ and $R_2$ have the same meanings as in formula I, with hydrogen in the presence of a hydrogenation catalyst, such as Raney nickel, platinum or palladium, or with a complex hydride, especially sodium borohydride.

If desired, a racemic mixture of a compound of the formula I obtained by the above-described methods of preparation may be separated into optical antipode components or diastereomeric antipode pair components thereof by conventional methods.

The compounds of the formula I are organic bases and therefore form acid addition salts with inorganic or organic acids by known methods. Examples of non-toxic, pharmacologically acceptable acid addition salts are those formed with hydrochloric acid, hydrobromic acid, sulfuric acid, benzoic acid, methanesulfonic acid, 8-chlorotheophylline or the like.

The following examples further illustrative the present invention and will enable others skilled in the art to understand it more completely. It should be understood, however, that the invention is not limited solely to the particular examples given below.

EXAMPLE 1

1-[(4'-Hydroxy-3'-dimethylaminosulfonamido)-phenyl]-1-hydroxy-2-(2''-phenoxyisopropylamino)-ethane hydrochloride by method A a. 155 gm of 4-benzyloxy-3-amino-acetophenone were reacted in 750 ml of pyridine with 110 gm of dimethylaminosulfochloride at 20° C to form 4-benzyloxy-3-dimethylaminosulfonamido-acetophenone, m.p. 109° C (recrystallized from ethanol). The yield was 215 gm.

b. 87 gm of the product obtained in (a) were reacted in 435 ml of chloroform with 12.5 ml of bromine at 60° C, the chloroform was distilled off, and the residue was caused to crystallize by treating it with isopropanol, yielding 81 gm of 4-benzyloxy-3-dimethylaminosulfonamido-ω-bromo-acetophenone, m.p. 110° C.

c. 40 gm of the product obtained in (b) were reacted in 150 ml of acetonitrile with 30.2 gm of 1-phenoxyisopropylamine, the reaction product was collected by vacuum filtration, the 1-phenoxyisopropylamine hydrobromide component of the filter cake was extracted with water, and the residual reaction product, 1-(4'-benzyloxy-3'-dimethylaminosulfonamido)-ω-(1''-phenoxyisopropylamino)-acetophenone, m.p. 130°-135° C, was reduced in ethanol with an excess of sodium borohydride to form a racemic mixture of 1-(4'-benzyloxy-3'-dimethylaminosulfonamido-phenyl)-1-hydroxy-2-(1''-phenoxyisopropylamino)-ethane. The isolated mixture of the diastereoisomeric bases was dissolved in ethyl acetate, and the solution was admixed with the calculated amount of ethereal hydrochloric acid, whereby 48% of theory of the hydrochloride of one of the diastereoisomers, m.p. 155°-156° C, precipitated out.

11 gm of the hydrochloride thus obtained were hydrogenated in 110 ml of methanol in the presence of Raney nickel as a catalyst until one equivalent of hydrogen had been absorbed, yielding 1-(4'-hydroxy-3'-dimethylaminosulfonamidophenyl)-1-hydroxy-2-(2''-phenoxyisopropyl-amino)-ethane hydrochloride, m.p. 186° C (recrystallized from isopropanol), of the formula

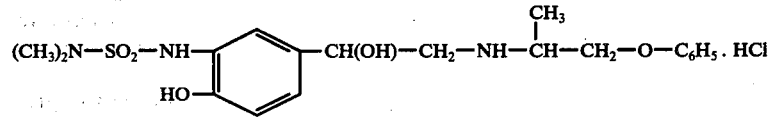

EXAMPLE 2

Using a procedure analogous to that described in Example 1 (c), 1-(4'-hydroxy-3'-dimethylaminosulfonamido-phenyl)-1-hydroxy-2-[2''-(p-hydroxyphenyl)-tert.butyl-amino]-ethane hydrochloride m.p. 183° C, of the formula

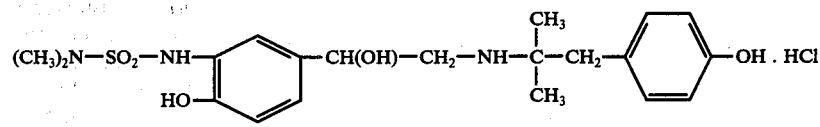 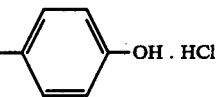

was prepared from 4-benzyloxy-3-dimethylaminosulfonamido-ω-bromo-acetophenone and 2-(p-acetoxyphenyl)-tert.butylamine. The acetyl group is split off during the reduction with sodium borohydride.

EXAMPLE 3

Using a procedure analogous to that described in Example 1(c), 1-(4'-hydroxy-3'-dimethylaminosulfonamido-phenyl)-1-hydroxy-2-(3''-naphthyl-tert.pentyl-amino)-ethane hydrochloride, m.p. 198°-201° C, of the formula

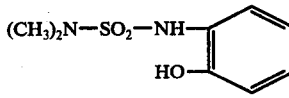 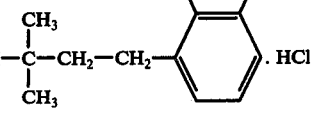

was prepared from 4-benzyloxy-3-dimethylaminosulfonamido-ω-bromo-acetophenone and 3-naphthyl-tert.-pentyl-amine.

EXAMPLE 4

Using a procedure analogous to that described in Example 1(c), 1-(4'-hydroxy-3'-dimethylaminosulfonamido-phenyl)-1-hydroxy-2-(3''-phenyl-tert.pentylamino)-ethane hydrochloride monohydrate, m.p. 90° C (decomp.), of the formula

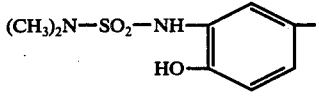 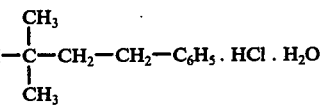

was prepared from 4-benzyloxy-3-dimethylaminosulfonamido-ω-bromo-acetophenone and 3-phenyl-tert.-pentyl-amine.

EXAMPLE 5

1-(4'-hydroxy-3-dimethylaminosulfonamido-phenyl)-1-hydroxy-2-(2''-p-hydroxyphenyl-isopropylamino)-ethane benzoate by method B 21.4 gm of 4-benzyloxy-3-dimethylaminosulfonamido-ω-bromo-acetophenone were reacted in 60 ml of acetonitrile with 24.1 gm of N-benzyl-N-(2-p-hydroxyphenyl-isopropyl)-amine and the N-benzyl-N-(2-p-hydroxyphenyl-isopropyl)-amine hydrobromide precipitated thereby was separated by vacuum filtration, and the acetonitrile was distilled out of the filtrate. The residual 4-benzyloxy-3-dimethylaminosulfonamido-ω-[N-benzyl-N-(2-p-hydroxyphenyl-isopropyl)-amino]-acetophenone was dissolved in 140 ml of methanol, and the resulting solution was admixed with 70 ml of water, 5 ml of concentrated hydrochloric acid, 10 ml of an aqueous 2% palladium chloride solution and activated charcoal. The mixture was hydrogenated at 60° C and 5 atmospheres gauge until both of the benzyl groups had been split off. The 4-hydroxy-3- dimethylaminosulfonamido-ω-(2'-p-hydroxyphenyl-isopropyl)amino-acetophenone hydrochloride, from ethanol, obtained thereby was hydrogenated in methanol at atmospheric pressure and room temperature in the presence of platinum oxide as a catalyst, yielding 1-(4'-hydroxy-3'-dimethylaminosulfonamido-phenyl)-1-hydroxy-2-(2''-p-hydroxyphenyl-isopropylamino)-ethane benzoate, m.p. 170° C (sintering beginning at 140° C), of the formula

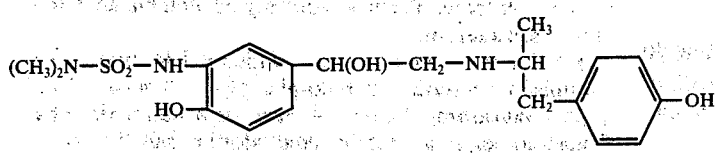

The compounds according to the present invention, that is, racemic mixtures, diastereoisomeric antipode pairs and optically active isomers of those embraced by formula I and non-toxic acid addition salts thereof, have useful pharmacodynamic properties. More particularly, the compounds of the instant invention produce a dilating effect upon the peripheral blood vessels, reduce the blood pressure, increase the cardiac output and, in addition, exhibit bronchospasmolitic activities in warm-blooded animals, such as cats, dogs and guinea pigs.

For pharmaceutical purposes the compounds according to the present invention are administered to warm-blooded animals perorally, parenterally or topically as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, aerosols, ointments, suppositories and the like. The effective single dosage unit range of the compounds according to the present invention is from 0.00083 to 1.67 mgm/kg body weight, depending upon route of administration, the dosage unit form and the indication. The oral dosage unit range is generally from 0.033 to 1.34 mgm/kg, preferably 0.083 to 0.34 mgm/kg. The parenteral dosage unit range is from about 0.0083 to 0.34 mgm/kg. In the case of aerosols, these are dispensed from suitable metering devices which expel about 0.05 to 2 mgm of active ingredient per actuation of the metering valve.

The following examples illustrate a few pharmaceutical dosage unit compositions comprising a compound of the present invention as an active ingredient and represent the bese mode contemplated of putting the invention into practical use. The parts are parts by weight unless otherwise specified.

EXAMPLE 6

Tablets

The tablet composition was compounded from the following ingredients:

| | |
|---|---|
| End product of Example 1 | 10 parts |
| Stearic acid | 6 " |
| Dextrose | 584 " |
| Total | 600 parts |

Preparation:

The ingredients were compounded in conventional manner, and the composition was compressed into 600 mgm-tablets in a conventional tablet making machine. For use as a bronchospasmolytic, the amount of active ingredient may be varied between 2 and 80 parts, the amount of dextrose being correspondingly increased or decreased, respectively.

EXAMPLE 7

Ointment

The ointment was compounded from the following ingredients:

| | | |
|---|---|---|
| End product of Example 3 | | 0.200 parts |
| Fuming hydrochloric acid | | 0.011 " |
| Sodium pyrosulfite | | 0.050 " |
| Mixture of equal parts of cetyl alcohol and stearyl alcohol | | 18.000 " |
| White vaseline | | 5.000 " |
| Synthetic bergamot oil | | 0.075 " |
| Distilled water | q.s.ad | 100.000 " |

The ingredients were compounded in conventional manner into an ointment, which was a topical pharmaceutical composition with effective dilating action on the peripheral blood vessels.

EXAMPLE 8

Inhalation aerosol

The aerosol was compounded from the following ingredients:

| | | |
|---|---|---|
| End product of Example 4 | | 0.20 parts |
| Soybean lecithin | | 0.05 " |
| Propellant gas mixture (Frigen 11, 12 and 14) | q.s.ad | 100.00 " |

The ingredients were compounded in conventional manner, and the composition was filled into aerosol containers with a metering valve, the valve being such that an amount of aerosol containing from 0.05 to 2.0 mgm of the active ingredient was expelled with each actuation.

Analogous results are obtained when any one of the other compounds embraced by formula I or a non-toxic, pharmacologically acceptable acid addition salt thereof is substituted for the particular active ingredient in Examples 6 through 8. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic mixture of a compound of the formula

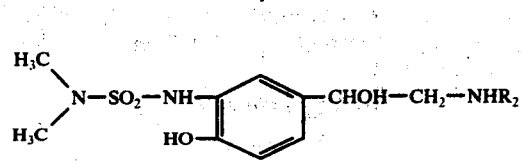

wherein $R_2$ is phenoxy-(alkyl of 3 carbon atoms), phenyl-(alkyl of 5 carbon atoms), or naphthyl-(alkyl of 5 carbon atoms);
a diastereoisomeric antipode pair thereof; an optically active isomer thereof; or a non-toxic, pharmacologically acceptable acid addition salt of said racemic mixture, antipode pair or optical isomer.

2. A compound of claim 1, wherein
$R_2$ is phenoxy-(alkyl of 3 carbon atoms),
or a non-toxic, pharmacologically acceptable acid addition salt thereof.

3. A compound of claim 1, wherein
$R_2$ is phenyl-(alkyl of 5 carbon atoms),
or a non-toxic, pharmacologically acceptable acid addition salt thereof.

4. A compound of claim 1, wherein
$R_2$ is naphthyl-(alkyl of 5 carbon atoms),
or a non-toxic, pharmacologicaly acceptable acid addition salt thereof.

5. A compound of claim 1, which is 1-(4'-hydroxy-3'-dimethylaminosulfonamido-phenyl)-11 -hydroxy-2-(2''-phenoxyisopropyl-amino)-ethane or a non-toxic, pharmacologically acceptable acid addition salt thereof.

* * * * *